United States Patent [19]

Sertich

[11] 4,283,174
[45] Aug. 11, 1981

[54] DENTAL SCALER HAVING SCALING TIP PARTICULARLY SUITABLE FOR CIRCULAR OR ELLIPSOIDAL PATTERNS OF VIBRATION

[76] Inventor: Anthony T. Sertich, 30 Dover Green, Staten Island, New York, N.Y. 10312

[21] Appl. No.: 91,013

[22] Filed: Nov. 5, 1979

[51] Int. Cl.³ .............................................. A61C 1/07
[52] U.S. Cl. .................................... 433/119; 433/165
[58] Field of Search ............... 433/118, 119, 165, 166; 51/59.55

[56] References Cited

U.S. PATENT DOCUMENTS

| | | | |
|---|---|---|---|
| 2,878,809 | 3/1959 | Treace | 433/165 |
| 2,990,616 | 7/1961 | Balamuth et al. | 433/119 |
| 3,133,351 | 5/1964 | Von Seggern | 433/119 |
| 3,368,280 | 2/1968 | Friedman et al. | 51/59.55 |
| 3,930,173 | 12/1975 | Banko | 433/119 |

Primary Examiner—Robert Peshock
Attorney, Agent, or Firm—John A. Dhuey; Joseph I. Hirsch

[57] ABSTRACT

A powered dental scaler is disclosed of a type which drives a vibrating scaling tip in a circular or ellipsoidal pattern of motion. A scaling tip having working surfaces provided by the edges of an elongated, curved element which has a cross-sectional configuration in the shape of a multi-sided figure, e.g., a triangle or a diamond, is particularly useful with a scaler having this type of vibrational pattern. The scaler tip also has a curved free end portion terminating in a point. These configurations enable a dental operator to conduct important dental cleaning operations with a single hand-held instrument.

23 Claims, 11 Drawing Figures

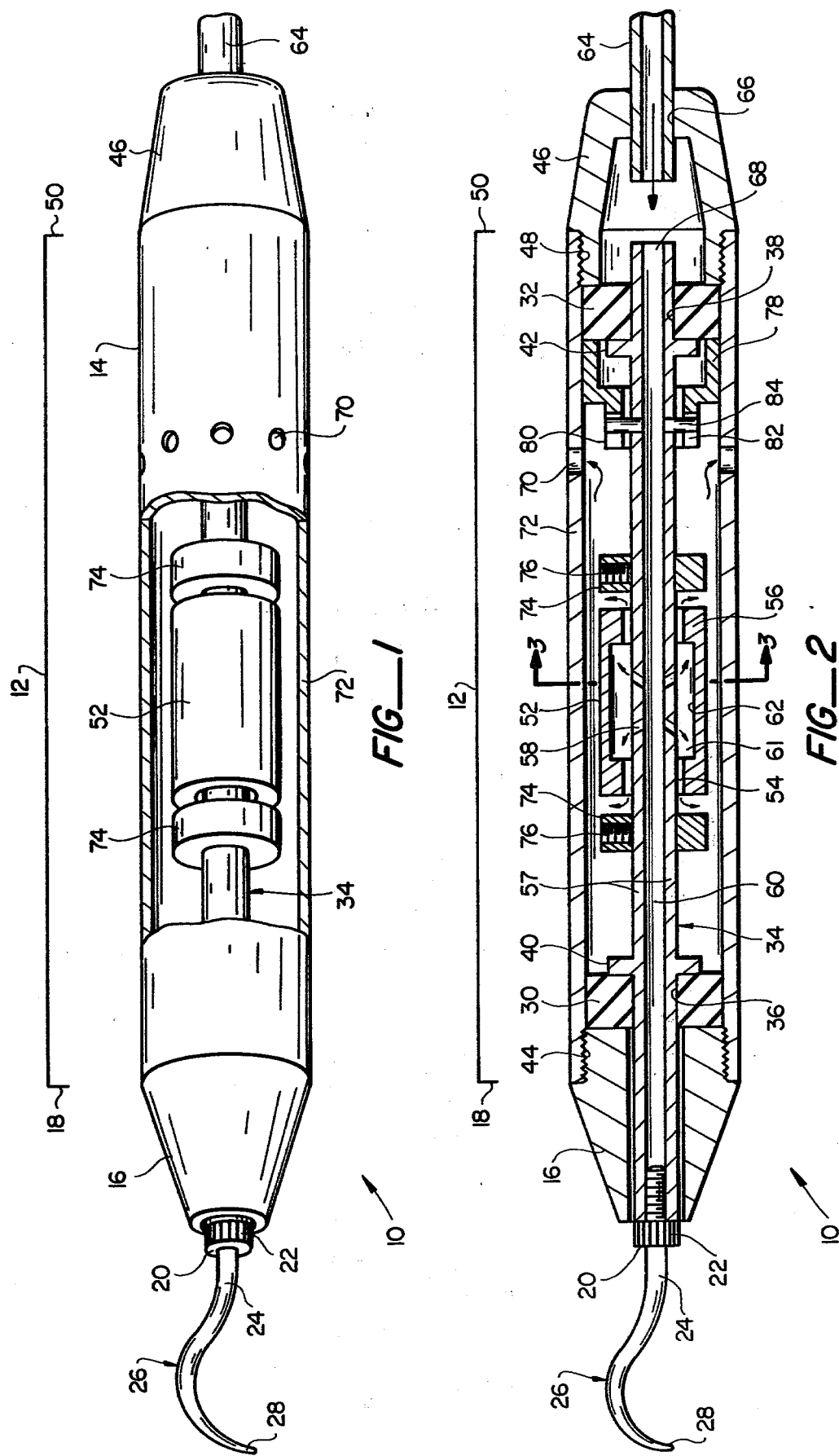

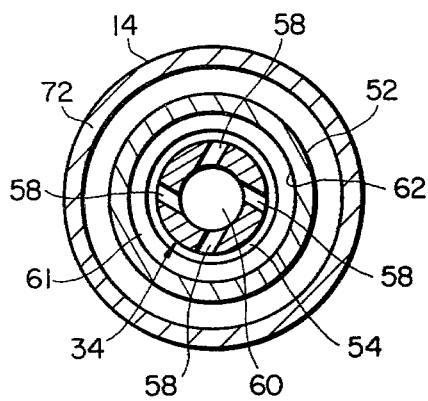
FIG_3
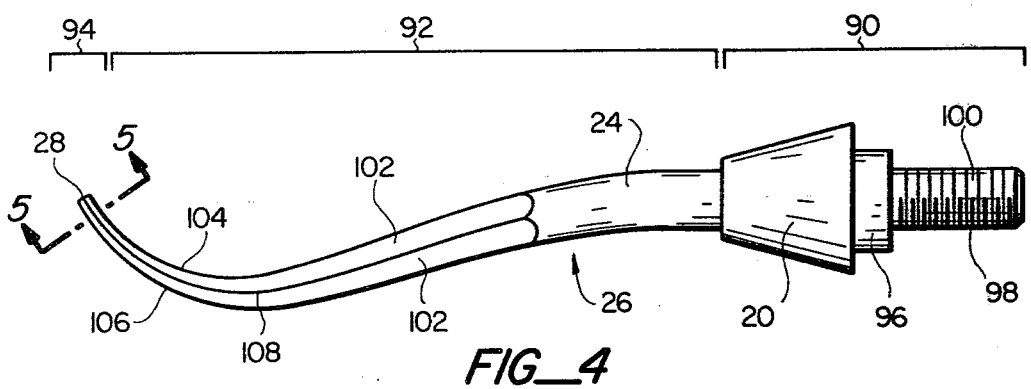
FIG_4
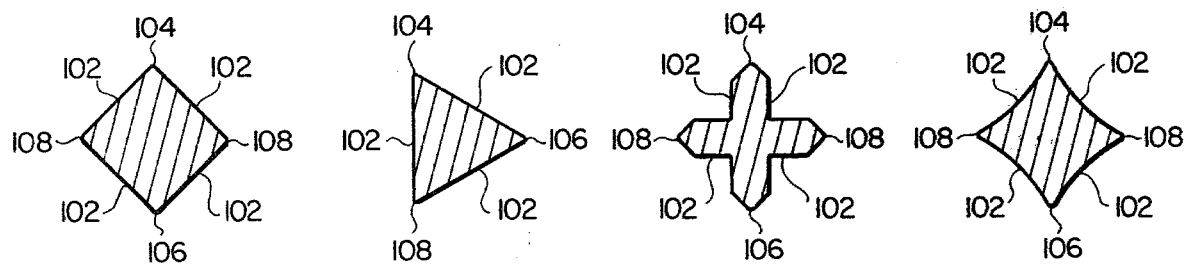
FIG_5A  FIG_5B  FIG_5C  FIG_5D
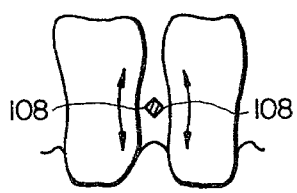 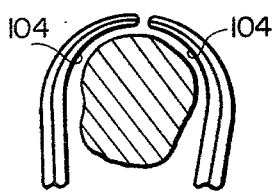 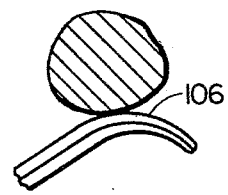
FIG_6  FIG_7A  FIG_7B

DENTAL SCALER HAVING SCALING TIP PARTICULARLY SUITABLE FOR CIRCULAR OR ELLIPSOIDAL PATTERNS OF VIBRATION

BACKGROUND OF THE INVENTION

Field

Power driven dental scalers are well known. Of particular interest herein is a dental scaler having a scaling tip with an improved work surface configuration.

State of the Art

Of the power driven dental scalers currently available, most common are scalers utilizing compressed air or an electrical ultrasonic transducer to cause the scraping type work tool to vibrate.

Typical of the earlier air-driven dental scalers are those of U.S. Pat. Nos. 3,820,529 and No. 3,444,622 to Mills et al, which scalers utilize an air-driven ball contained in a chamber. Movement of the ball against the walls of the chamber imparts vibration to the chamber which vibrations are then transmitted to the scraping tool. A more recent type of air-driven scaler, described in U.S. Pat. No. 3,526,962 to Fuerst, utilizes a rotatable mandrel which has an irregularly-shaped tip engaged with a reciprocable block in which the mandrel tip is received.

It is characteristically a problem of these air driven scalers that much of the vibrational energy generated by the vibrator motor is transferred to the handle portion of the dental scaler rather than to the scraper work tool. Moreover, the modes of vibration of these scalers may change as moving parts of the vibration generating mechanism wear with time.

In U.S. Pat. No. 3,703,037 to Robinson, there is described a dental scaler which utilizes an electrical ultrasonic transducer to provide constant modes of vibration for coupling with particular types of work tools. One disadvantage of the ultrasonic scaler, however, is the cost of the transducer and its associated ultrasonic generator.

A recent improvement in air-driven dental scalers is disclosed in U.S. Pat. No. Re. 29,687 to Sertich. This dental scaler has very few moving parts as compared to the aforementioned mechanically complicated air-driven scalers and provides efficient transfer of vibrational energy to a scraping-type work tool with relatively little vibration being transferred to the handle portion of the instrument. Moreover, the Sertich-type scaler provides uniform modes of constant vibration which may be matched with the vibratory modes of various types of work tools without the need for any complicated electronic components.

The Sertich-type dental scaler achieves these advantages in part by including a single, rigid vibratable tube mounted on resilient support washers disposed at or near the theoretical vibratory nodes characteristic of the natural vibrational mode of the tube. A work tool, such as a scraper or a pick, is typically secured to the working end of the vibratable tube by a connection between an externally-threaded work tool shank and an internally threaded portion of the tube.

The mode or pattern of vibration of the vibratable tube of the Sertich-type scaler is characteristically one which during one oscillation or cycle of vibration traces a path that may vary from circular to oval or ellipsoidal in shape. It has been found that this particular vibratory orbit provides maximum efficiency of energy transfer from the tube vibrating mechanism to the working tip.

There has been some attention given to the matching of vibratory mode to a particular scaler tip configuration. For example, in U.S. Pat. No. 2,990,616 to Balamuth et al there is described a preferred mode of vibration which is elliptical in configuration. The described elliptical motions of a tapered vibrating tip provide efficient cutting action for forming a hollowed out portion in a hard, dense material such as tooth dentin. The Balamuth patent discloses one tip configuration for use by a dentist in boxing, that is, in preparing cavities of rectangular cross-section. The tip has an arcuate, somewhat tapered shank and is square in cross-section near the working end of the tip. One problem with the Balamuth tip, however, is that it lacks sufficient curvature, particularly at its working end to perform many of the necessary cleaning functions around tooth edges and hollows.

There is, therefore, a need for a novel scaler tip for use with a dental scaler having an efficient vibratory mode which provides a scaling action best suited for removing calculus and stain.

SUMMARY OF THE INVENTION

A rigid dental scaler tip is provided having an operative end and an end adapted to be secured to a handheld dental scaler, the operative end terminating in a curved free end, the operative end having a plurality of sides extending over a portion of the working end, a perpendicular cross-section of the operative end at any point along the working dimension thereof being a multi-sided figure, the curved free end lying in the plane passing through the longitudinal dimension of the scaler tip.

The scaler tip of the invention is particularly suitable for use as a work tool connected to an air driven dental scaler comprising elongated casing means having a proximal end and a distal end, resilient support means within the casing means, a substantially rigid shaft within the elongated casing means, the shaft supported within the casing means by the resilient support means, and means for imparting vibration to the resiliently supported shaft to provide vibratory movement to a work tool connected to the shaft. The multi-sided figure can be triangular or diamond shaped. Moreover, the operative end of the tip is symmetrical about a plane passing through the longitudinal dimension of the tip. In such a configuration the defined plane passes through two opposed junctions each formed by the intersection of a different pair of two of four sides of the tip. Two of the four sides intersect with each other to form a first junction extending along the inner radius of the curved operative end. The other two of the four sides then intersect with each other to form a second junction, opposite the first junction, extending along the outer radius of the operative end. The first and second junctions will lie along a plane passing through the longitudinal dimension of the scaler tip and on which the curved free end lies.

In an alternate embodiment, the sides forming the multi-sided figure are formed with relieved surfaces to provide two working edges which can simultaneously impact on deposits on teeth and facilitate removal of those deposits.

The means for imparting vibration to the resiliently supported rigid shaft to provide vibratory movement to the work tool connected to the rigid shaft can be of a type disclosed in the aforementioned U.S. Pat. No. Re. 29,687, which is incorporated herein by reference.

One advantage provided by the scaler of the present invention is that both efficient scaling action and cleaning are provided in one tool which is of significant convenience to a dental operator.

DESCRIPTION OF SPECIFIC EMBODIMENTS

The means providing the features and advantages of the present invention are illustrated in the accompanying drawings wherein:

FIG. 1 is a perspective view, partly in section, of a dental scaling instrument;

FIG. 2 is a longitudinal cross-sectional view of the dental scaler of FIG. 1;

FIG. 3 is a cross-sectional view of the vibratory driving mechanism of the dental scaler of FIG. 2 taken along line 3—3;

FIG. 4 is a side elevational view of a scaler tip of this invention;

FIG. 5A, is a cross-sectional view of the scaler tip of FIG. 4 taken along line 5—5;

FIGS. 5B, 5C and 5D are cross-sectional views (similar to that of FIG. 5A) illustrating alternate cross-sectional configurations for the scaler tip of this invention;

FIG. 6 is a side elevational view of a pair of human incisor teeth with the scaler tip of FIGS. 4 and 5A shown in section, positioned therebetween; and FIGS. 7A, and B are top sectional views of teeth showing various uses of a scaler tip of this invention.

Illustrated in FIG. 1 is a dental scaling instrument 10 comprising a handle 12 which includes a barrel 14 and a neck 16. Attached to the distal end 18 of handle 12 is a nose piece 20 having an outer knurled wall 22. Secured within nose piece 20 is a shank 24 of a work tool 26 having a configuration of a curved scaler tip having a terminal or free end 28. As shown in detail in the cross-sectional view of FIG. 2, handle 12 provides an elongated housing or casing within which are mounted resilient support means comprising a first or front resilient support bushing 30 and a second or rear resilient support bushing 32. Disposed substantially coaxially with respect to elongated handle 12 is a vibratable shaft in the form of a tube 34 which passes through axially disposed openings 36 and 38, respectively, in bushings 30 and 32. Substantial axial movement of tube 34 is prevented by first and second flanges 40 and 42 which rest against bushings 30 and 32, respectively. First support bushing 30 is retained within the elongated casing by neck 16 which is threadedly engaged with inner wall portion 44 at distal end 18 of handle 12. Similarly, cap 46, which is threadedly engaged with inner wall portion 48 at proximal end 50, retains second support bushing 32 within the elongated casing provided by handle 12.

Disposed about a mid-portion of tube 34 is a sleeve-like rotor 52. As shown in FIG. 2, rotor 52 is disposed substantially coaxially with respect to tube 34, there being annular gaps 54 established between annular-shaped end portions 56 of rotor 52 and adjacent portions of side wall 57 of tube 34. In an actual assembly with rotor 52 at rest, rotor 52 will be supported upon tube 34 so that a portion of each of the annular ends 56 will rest upon side wall portions of tube 34. Located in side wall portions of tube 34 is a plurality of outlet ports 58 which connect passageway 60 of tube 34 to a chamber 61 defined by inner wall 62 of rotor 52 and an adjacent portion of tube side wall 57.

As indicated by the arrows in FIG. 2, a fluid medium, such as compressed air, is supplied from a source (not shown) through a supply tube 64 which passes through an axially disposed opening 66 in cap 46. The flow of compressed air passes into fluid media inlet port 68 and through passageway 60 to fluid media outlet ports 58. The flow of compressed air which exhausts through outlet ports 58 fills chamber 61. The force of impact of the air on inner wall 62 of rotor 52 urges rotor 52 to rotate rapidly about tube 34. As shown in FIG. 3, each of outlet ports 58 has an axis which is offset or spaced at a distance from the longitudinal axis of tube 34, such that each port axis does not intersect the axis of tube 34. Thus each of ports 58 directs a jet of air at a glancing angle with respect to the inner wall 62 of rotor 52 so as to impart rotary movement to rotor 52. Also, as shown in FIG. 2, outlet ports 58 are preferably angled with respect to a plane which is perpendicular to tube 34 and which bisects rotor 52, so that air discharged from half of the plurality of ports 58 imparts a component of force tending to move rotor 52 in the distal direction, while flows of air discharged from the other half of the plurality of ports 58 impart a component of force tending to move rotor 52 in the proximal direction.

After imparting rotary movement to rotor 52, the air exhausts from chamber 61 through fluid media outlet ports as provided by annular gaps 54 defined by annular end portions 56 and tube side wall 57. The air is further exhausted from the interior of barrel 14 through exhaust ports 70 disposed circumferentially about a rearward portion 72 of barrel 14. Stop means comprising annular-shaped guides 74 are affixed to tube 34 by set screws 76. Guides 74 are positioned adjacent either end of rotor 52 so as to limit movement of rotor 52 in the axial direction along tube 34.

The speed of revolution of rotor 52 about tube 34 is generally dependent upon the size, number and angles of incidence of the air streams discharged from outlet ports 58, and the velocity thereof. A description of the manner in which the spinning rotor 52 imparts vibration to tube 34 may be found in the aforementioned U.S. Pat. No. Re. 29,687.

It is generally characteristic of the various Sertich-type dental scalers that the mode of vibration as evidenced by a trace of movement of a cross-section of tip 26, taken as shown in FIG. 5, may vary from a circular to an ellipsoidal pattern. The particular pattern traced and the amplitude of vibration is believed to be dependent upon the mass of tip 26, its configuration in cross-section, the vibratory mode of tube 34 and the amount of energy transferred to tip 26 from tube 34.

As shown in FIG. 4, scaler tip 26 has a connectable end portion 90 adapted to be secured to a dental instrument, a working free end portion 94 and a working mid-portion 92. End portion 90 comprises a nose piece or finger grip 20 having a boss portion 96 to which is affixed a stud 98 having a threaded portion 100. Threaded portion 100 operatively secures scaler tip 26 to tube 34. Scaler mid-portion 92 includes a shank 24 having a generally circular cross-section and which extends into and is frictionally engaged with nose piece 20. Shank 24 comprises about one-quarter the length of mid-portion 92, the balance of mid-portion 92 having a curved, elongated configuration with a plurality of sides 102. A cross-section taken at any point along and substantially perpendicular to the longitudinal axis of scaler mid-portion 92 has a configuration of an equilateral, multi-sided figure. As shown in FIG. 5A, the cross-section has the shape of a diamond, that is, a square tilted on one of its edges. Alternate cross-sections are shown in FIGS. 5B, 5C and 5D, illustrating triangular, cruciform and relieved square configurations, respectively.

Scaler tip 26 also includes a curved working fee end portion 94 having a terminal end 28, as shown in FIG. 4. The curved free end portion 94 generally lies in a plane passing through the longitudinal dimension of scaler tip 26 and can be symmetrical about that plane. Free end 94 and a part of mid-portion 92 are curved so as to form a concave working edge 104 as provided by a first junction or intersection of two adjacent sides 102 and a convex working edge 106 as provided by a second junction or intersection of two other adjacent sides 102, the first and second junctions being in opposed relationship. The described plane of symmetry will thus preferably pass through the two opposed junctions formed by the intersection of different pairs of two of four sides 102. A pair of lateral working edges 108 is provided by opposed third and fourth junctions or intersections as established by the junctions of pairs of opposed sides 102, portions of which third and fourth junctions lie in a plane substantially perpendicular to the first defined plane containing the free end.

Scaler tip free end portion 94 has a terminal end 28 formed by sides 102 which taper in width toward terminal 28 and by the converging of concave edge 104, convex edge 106 and lateral edges 108.

The described scaler tip of the invention provides in one work tool several advantageous features. For example, as shown in FIG. 6, lateral edges 108 provide symmetrical scaling on all sides of a tooth and especially provide very good interproximal scaling. It is especially an advantage of the present invention that the circular or ellipsoidal motion of the scaler tip, in combination with the diamond-shaped cross-sectional configuration, provides very efficient and uniform scaling action of deposits from teeth. A second feature of the scaler tip is provided by the curved work surfaces. The curved part of mid-portion 92 is substantially greater in length than free end 94 and facilitates scaling of deposits from teeth. For example, concave working edge 104 allows cleaning of the sharp curves of teeth as depicted in FIG. 7. Concave edge 104 is suited for cleaning the contours of molars, as shown in FIG. 7A. Convex edge 106 is useful for removing stain from anterior buccal surfaces as shown in FIG. 7B. A third advantage of the scaler tip of this invention is provided by terminal 28 which is useful for removing stain and debris from small tooth recesses.

In an alternate embodiment of the invention, surfaces 102 adjacent terminal end 28 of free end portion 94 are relieved between the junctions formed by the intersection of adjacent surfaces 102. As shown particularly in FIG. 5C and FIG. 5D, surfaces 102 can be relieved to present working edges 104, 106 and 108, two of which can simultaneously impact on tooth deposits upon appropriate manipulation of tip 26. Simultaneous impaction with two edges greatly increases the stresses in deposits and facilitates the rapid removal thereof. Surface relief can be produced by grooving surfaces 102 to form the cruciform shape of tip 26 illustrated in FIG. 5C. In another embodiment illustrated in FIG. 5D, surface relief is not as severe and surfaces 102 are hollow ground to provide the appropriate working edges.

The tips of this invention can be utilized with a dental scaler or vibratory device of the type described in Sertich Pat. No. Re. 29,687 or copending application Ser. No. 91,016, entitled "Rotor Driven Vibratory Device Having Rotor Centralization Means and Vibrational Mode Selection Means Associated Therewith," filed concurrently herewith. If desired, such a dental scaler or vibratory device can be modified in accordance with the teachings of any or all of copending applications Ser. Nos. 12,631, filed Feb. 16, 1979; 26,378, filed Apr. 2, 1979; and application Ser. No. 91,012, entitled "Vibratory Device Having Tool Assembly With Fluid Transport Means," filed concurrently herewith. The above applications are incorporated herein by reference to the extent necessary to supplement or complete the disclosure hereof.

While this invention has been described with reference to specific embodiments thereof, it should be understood by those skilled in this art that various changes may be made and equivalents may be substituted without departing from the true spirit and scope of the invention. All such modifications are intended to be within the scope of the claims appended hereto.

What is claimed is:

1. A dental scaler comprising:

elongated casing means having a proximal end and a distal end;

resilient support means within said casing means;

a rigid shaft supported within said elongated casing means by said resilient support means;

means for imparting vibration to said resiliently supported rigid shaft when said scaler is energized to provide vibratory movement to a work tool connected to said rigid shaft; and a work tool connected to the distal end of said rigid shaft, said work tool comprising a rigid shank having an operative end and an end adapted to be connected to said rigid shaft, said operative end terminating in a curved free end, said operative end having a plurality of generally planar sides extending over a portion of the length thereof, a perpendicular cross-section of said operative end at any point along said portion thereof being a multi-sided figure, said curved free end lying in a plane passing through the longitudinal dimension of said work tool, said operative end being symmetrical about the plane passing through the longitudinal dimension of said work tool, the plane also passing through at least one junction formed by the intersection of an adjacent pair of two of said sides.

2. The dental scaler of claim 1 wherein said figure is four-sided.

3. The dental scaler of claim 2 wherein said figure is diamond-shaped.

4. The dental scaler of claim 2 wherein two of said four sides intersect with each other to form a first junction extending along the inner radius of said curved free end; the other two of said four sides intersect with each other to form a second junction, opposite said first junction, extending along the outer radius of said curved free end; and said first and second junctions lie substantially along the plane passing through the longitudinal dimension of said work tool and on which said curved free end lies.

5. The dental scaler of claim 4 wherein two of said four sides intersect with each other to form a third junction extending generally parallel to said first and second junctions; the other two of said four sides intersect with each other to form a fourth junction extending generally parallel to said first and second junctions and opposite said third junction; and portions of said third and fourth junctions lie along a plane substantially perpendicular to the plane passing through the longitudinal dimension of said work tool on which said curved free end lies.

6. The dental scaler of claims 4 or 5 wherein said figure is diamond-shaped.

7. The dental scaler of claim 1 wherein said figure is three-sided.

8. The dental scaler of claim 1 wherein said means for imparting vibration to said resiliently supported rigid shaft comprises means for imparting vibratory movement to said shaft so that said work tool vibrates in a mode substantially tracing an ellipsoidal-shaped or circular path.

9. The dental scaler of claim 8 wherein said rigid shaft comprises a tube supported along spaced apart portions thereof by said resilient support means, said tube including fluid media inlet means and outlet means, respectively for receiving and discharging fluid media;

said means for imparting vibration comprises rotor means operatively associated with said tube and disposed axially parallel with respect to the axis of said tube, said rotor means drivable about said tube by the fluid media;

said tube and said rotor means each having a configuration and disposed with respect to each other so as to define a space therebetween for receiving the fluid media during movement of said rotor means with respect to said tube;

whereby fluid media flowing through said inlet means into the space drives said rotor means rotatably with respect to said tube so that said rotor means imparts vibratory movement to said tube.

10. The dental scaler of claim 9 wherein said fluid media inlet means comprises an opening in one end of said tube adjacent the proximal end of said casing;

said fluid media outlet means comprises one or more ports in the sidewall of said tube, each of said ports having an axis spaced from the longitudinal axis of said tube;

said rotor means is a sleeve having an inner diameter slightly greater than the outer diameter of said tube, and said sleeve is disposed with respect to said tube so that one or more of said tube outlet ports may discharge fluid media into the space between said sleeve and said tube.

11. A rigid dental scaler tip having an operative end and an end adapted to be secured to a hand-held dental scaler, said operative end terminating in a curved free end, said operative end having a plurality of sides extending along a portion of the length thereof, a perpendicular cross-section of said operative end at any point along said portion thereof being a multi-sided figure, said curved free end lying in a plane passing through the longitudinal dimension of said scaler tip, said operative end being substantially symmetrical about the plane passing through the longitudinal dimension of said tip, the plane also passing through at least one junction formed by the intersection of a pair of two of said sides.

12. The tip of claim 11 wherein said figure is four-sided.

13. The tip of claim 12 wherein said figure is diamond-shaped.

14. The tip of claim 12 wherein two of said four sides intersect with each other to form a first junction extending along the inner radius of said curved free end; the other two of said four sides intersect with each other to form a second junction, opposite said first junction, extending along the outer radius of said curved free end; and said first and second junctions lie substantially along the plane passing through the longitudinal dimension of said scaler tip and on which said curved free end lies.

15. The tip of claim 12 wherein two of said four sides intersect with each other to form a third junction extending generally parallel to said first and second junctions; the other two of said four sides intersect with each other to form a fourth junction extending generally parallel to said first and second junctions and opposite said third junction; and portions of said third and fourth junctions lie along a plane substantially perpendicular to the plane passing through the longitudinal dimension of said scaler tip on which said curved free end lies.

16. The tip of claims 14 or 15 wherein said figure is diamond-shaped.

17. The tip of claim 11 wherein said figure is three-sided.

18. A dental scaler tip having an operative end and an end adapted to be secured to a hand-held dental scaler, said operative end terminating in a curved free end, said operative end having a plurality of sides extending along a portion of the length thereof, a perpendicular cross-section of said operative end at any point along said portion thereof being a multi-sided figure, at least one side of said plurality of sides adjacent the terminal end of said curved free end having a relieved surface intermediate the junctions formed by the intersection of adjacent sides.

19. The scaler tip of claim 18 wherein said curved free end lies substantially in a plane passing through the longitudinal dimension of said scaler tip.

20. The scaler tip of claim 19 wherein said multi-sided figure has four sides and said operative end is substantially symmetrical about the plane passing through the longitudinal dimension of said tip, the plane also passing through two opposed junctions each formed by the intersection of a different pair of two of said four sides, each of said four sides adjacent the terminal end of said curved free end having a relieved surface intermediate the junctions formed by the intersection of adjacent sides.

21. A dental scaler comprising:

elongated casing means having a proximal end and a distal end;

resilient support means within said casing means;

a rigid shaft supported within said elongated casing means by said resilient support means;

means for imparting vibration to said resiliently sypported rigid shaft when said scaler is energized to provide vibratory movement to a work tool connected to said rigid shaft; and a work tool connected to the distal end of said rigid shaft, said work tool comprising a rigid shank having an operative end and an end adapted to be connected to said rigid shaft, said operative end terminating in a curved free end said operative end having a plurality of sides extending along a portion of the length thereof, a perpendicular cross-section of said operative end at any point along said portion being a multi-sided plurality of sides adjacent the terminal end of said curved free end having a relieved surface intermediate the junctions formed by the intersection of adjacent sides.

22. The dental scaler of claim 21 wherein said curved free end lies substantially in a plane passing through the longitudinal dimension of said work tool.

23. The dental scaler of claim 21 wherein said multi-sided figure has four sides and said operative end is substantially symmetrical about the plane passing through the longitudinal dimension of said tip, the plane also passing through two opposed junctions each formed by the intersection of a different pair of two of said four sides, each of said four sides adjacent the terminal end of said curved free end having a relieved surface intermediate the junctions formed by the intersection of adjacent sides.

* * * * *